United States Patent [19]

Pews

[11] Patent Number: 4,929,268

[45] Date of Patent: May 29, 1990

[54] SUBSTITUTED OXIRANE COMPOUNDS

[75] Inventor: R. Garth Pews, Midland, Mich.

[73] Assignee: The Dow Chemical Company, Midland, Mich.

[21] Appl. No.: 716,861

[22] Filed: Mar. 27, 1985

[51] Int. Cl.$^5$ .......................................... A01N 43/00
[52] U.S. Cl. ........................................ 71/88; 549/553
[58] Field of Search ............................ 71/88; 549/553

[56] References Cited

U.S. PATENT DOCUMENTS

| | | | |
|---|---|---|---|
| Re. 29,826 | 11/1978 | Konya et al. | 71/105 |
| 2,472,347 | 6/1949 | Sexton | 71/105 |
| 2,859,239 | 11/1958 | Trapp et al. | 71/105 |
| 2,863,753 | 12/1958 | Wain | 71/105 |
| 3,063,822 | 11/1962 | Soper | 71/105 |
| 3,251,875 | 5/1966 | Gerjovich et al. | 71/105 |
| 3,277,171 | 10/1966 | Hopkins | 71/105 |
| 3,318,947 | 5/1967 | Speziale et al. | 71/119 |
| 3,457,063 | 7/1969 | Neighbors | 71/105 |
| 3,489,784 | 1/1970 | Fellig et al. | 71/105 |
| 3,719,465 | 3/1973 | Ozretich | 71/88 |
| 3,930,835 | 1/1976 | Ozretich | 71/88 |
| 4,013,772 | 3/1977 | Ozretich | 424/278 |
| 4,018,801 | 4/1977 | Ozretich | 424/278 |
| 4,211,549 | 7/1980 | Markley et al. | 71/88 |

FOREIGN PATENT DOCUMENTS 2115408A 9/1983 United Kingdom .

OTHER PUBLICATIONS

E. J. Corey et al., J. Am. Chem. Soc. (1962), vol. 84, pp. 3782–3783.
E. J. Corey et al., J. Am. Chem. Soc. (1965), vol. 87(6), pp. 1353–1364.
G. P. Butke et al., J. Org. Chem., vol. 43(5) (1978), pp. 954–960.
I. Prei-Bar et al., J. Org. Chem., vol. 48(24) (1983), pp. 4629–4634.
H. Kimoto et al., Bull. Chem. Soc. Japan, vol. 49(6) (1976), pp. 1642–1649.
A. Ranjon, Bull. Soc. Chim. Fr. (1971) (6), pp. 2068–2072.

Primary Examiner—Glennon H. Hollrah
Attorney, Agent, or Firm—S. Preston Jones; Ronald G. Brookens

[57] ABSTRACT

Herbicidal compositions and methods utilizing novel substituted oxirane compounds as active ingredients are disclosed.

18 Claims, No Drawings

SUBSTITUTED OXIRANE COMPOUNDS

SUMMARY OF THE INVENTION

This invention relates to herbicidal compositions and methods utilizing novel substituted oxirane compounds as active ingredients. According to the present invention, there are provided herbicidal compositions containing as the active ingredient compounds of the Formula

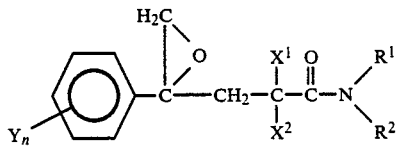

wherein
Y represents halogen, —CF$_3$ or methyl;
n represents an integer from 1 to 5, inclusive;
X$^1$ and X$^2$ independently represent chlorine, fluorine, bromine or iodine; and
R$^1$ and R$^2$ independently represent
  hydrogen,
  cyano,
  loweralkyl,
  cycloalkyl,
  aryl,
  aralkyl,
  —COOR (wherein R represents hydrogen or lower alkyl) or
  —CONZ$^1$Z$^2$ wherein
    Z$^1$ and Z$^2$ independently represent
    hydrogen,
    cyano,
    loweralkyl,
    cycloalkyl,
    aryl or
    aralkyl.

The present invention provides a method for killing and controlling both broadleaf and grassy weeds. An advantage of the present invention is the killing of weeds by either postemergence or preemergence application of the oxirane compounds to the locus of the weeds or weed seeds. Another advantage of the present invention is the selective control it provides of broadleaf and grassy weeds in the presence of economically important crops such as soybeans, cotton, white winter wheat, corn, sugar beets, rape, and cultivated rice. And still yet another advantage of the present invention is the excellent control it provides for weeds such as nutsedge, pigweed, crabgrass, Johnsongrass, barnyard grass, wild oats, yellow foxtail and morning glory.

DETAILED DESCRIPTION OF THE INVENTION

The term "herbicide" is used herein to mean a chemical compound or composition thereof used to control, suppress, or kill plants, or to severely interrupt their normal growth processes, as defined in the Herbicide Handbook of the Weed Science Society of America, 5th Edition, (1983), 309 West Clark Street, Champaign, Ill.

By "growth controlling" or "herbicidally-effective amount" is meant an amount of active ingredient which causes a modifying effect on plants and includes deviations from natural development, killing, regulation, dessication, retardation, and the like.

The term "plants" is meant to include germinating seeds, emerging seedlings and established vegetation.

The terms "active ingredient" or "active material" are defined as the chemical in a herbicide formulation primarily responsible for its phytotoxicity.

By "preemergence" is meant the application of the herbicidal compound to the soil prior to emergence of the specified weed or crop.

By "postemergence" is meant the application of the herbicidal compound to the plant after the emergence of the specified weed or crop.

The term "loweralkyl" is used in the present specification and in the appended claims to designate a straight or branched saturated hydrocarbon moiety (i.e. hydrocarbons having carbon-carbon single bonds) containing from 1 to about 6 carbon atoms, such as for example, methyl, ethyl, propyl, isopropyl, butyl, isobutyl, tert-butyl, pentyl, hexyl and the like.

The term "cycloalkyl" is employed herein to mean an alkyl moiety characterized by one or more closed rings and containing from 3 to about 8 carbon atoms, such as, for example, cyclopropyl, cyclobutyl, cyclopentyl, cyclohexyl, cycloheptyl, cyclooctyl and the like.

The term "aryl" or "Ar" designates an aromatic moiety such as phenyl and substituted phenyl. Substituted phenyl includes but is not limited to lower alkylphenyl such as methylphenyl, dimethylphenyl, trimethylphenyl, ethylphenyl, diethylphenyl, triethylphenyl, methylethylphenyl, dimethylethylphenyl, propylphenyl, butylphenyl, pentylphenyl, hexylphenyl; and halophenyl, such as mono, di, tri, tetra or pentahalo.

The terms "halogen" and "halo" as employed herein, represent chlorine, fluorine, bromine and iodine.

The term "aralkyl" designates an aryl moiety bonded to a loweralkyl moiety, such as, for example, phenylmethyl, diphenylmethyl, triphenylmethyl, phenylethyl, diphenylethyl, triphenylethyl, phenylpropyl, phenylbutyl, phenylpentyl, phenylhexyl and the like.

In the present specification and claims the term "sterically compatible" is employed to designate Y, R$^1$ and R$^2$ substituent groups which are not affected by steric hindrance as defined in "the Condensed Chemical Dictionary", 7th Edition, Reinhold Publishing Co., N.Y., page 893 (1966) which definition is as follows:

"steric hindrance. A characteristic of molecular structure in which the molecules have a spatial arrangement of their atoms such that a given reaction with another molecule is prevented or rewarded in rate."

Steric hindrance may be further defined as compounds having substituents whose physical bulk does not require confinement within volumes insufficient for the exercise of their normal behavior as discussed in "Organic Chemistry" of D. J. Cram and G. Hammon, 2nd Edition, McGraw-Hill Book Co., N.Y., page 215 (1964).

The active ingredients of the present invention are generally oils or crystalline solids at ambient temperatures and are soluble in many organic solvents commonly employed as herbicidal carriers. Active ingredients of the above Formula (I) wherein each Y group is the same constitute a preferred embodiment. The active ingredients wherein each Y is chlorine constitute a further preferred embodiment of the present invention. An additional preferred class of compounds are those in which Y is —CF$_3$. Preferably, n is an integer from 1 to 3; most preferably n is 1 or 2. Also preferred are embodiments where Y is substituted at the 3 or at the 3 and 5 positions. A preferred class are those compounds where X$^1$ and X$^2$ are both fluorine. An especially preferred class are those compounds where Y, X$^1$ and X$^2$ are each chlorine. Another especially preferred class are those compounds where R$_1$ and R$^2$ are both hydrogen. Especially preferred compounds include:

N-(aminocarbonyl)-α,α-dichloro-2-(3,5-dichlorophenyl)oxiranepropanamide;

(2,2-dichloro-3-(2-(3,5-dichlorophenyl)oxiranyl)-1-oxopropyl)carbamic acid, ethyl ester;

α,α-dichloro-N-cyano-2-(3,5-dichlorophenyl)-N-(1-methylethyl)oxiranepropanamide;

α,α-dichloro-2-(3,5-dichlorophenyl)-N-(2,6-diethylphenyl)oxiranepropanamide;

α,α-dichloro-2-(3,5-dichlorophenyl)-N-methyl-N-((methylamino)carbonyl)oxiranepropanamide;

α,α-dichloro-2-(3,5-dichlorophenyl)-N-(1,1-dimethylethyl)oxiranepropanamide;

2-(3,5-dichlorophenyl)-α,α-difluoro-oxiranepropanamide;

α,α-dichloro-2-(3-chlorophenyl)-oxiranepropanamide;

α,α-dichloro-2-(3,5-dichlorophenyl)-N-(phenylmethyl)oxiranepropanamide;

α,α-dichloro-N-(phenylmethyl)-2-(3-(trifluoromethyl)phenyl)oxiranepropanamide;

most preferably

α,α-dichloro-2-(3,5-dichlorophenyl)-oxiranepropanamide.

The active ingredients of the above Formula (I) are readily prepared by the reaction of a substituted styrene compound of the Formula

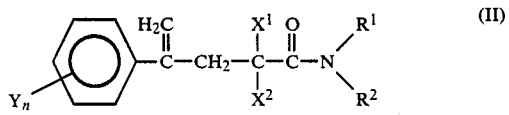

(II)

wherein Y$_n$, X$^1$, X$^2$, R$^1$ and R$^2$ are as defined hereinbefore, with a suitable percarboxylic acid reactant, as described for related compounds in U.S. Pat. No. 3,930,835 incorporated herein by reference.

Representative and suitable percarboxylic acids which can be employed in the preparation of the active ingredients include, for example, perchloracetic acid, pertrifluoroacetic acid, perbenzoic acid, peracetic acid, monochloroperbenzoic acid and the like. In preparing the compounds of the present invention, either nonaqueous or aqueous buffer mixtures can be employed and are prepared by the use of an alkaline buffering agent, such as, for example, sodium carbonates, bicarbonates and the like. The carbonates and bicarbonates can be also employed as a slurring in a heterogeneous fashion, as a mixture partially solid and partially liquid.

In carrying out the reaction, the substituted styrene compound of Formula (II) in a reaction medium, such as, for example, methylene chloride, chloroform, 1,2-dichlorobenzene and the like, is mixed slowly with the percarboxylic acid reactant in a buffer solution. While the amounts of the reactants to be employed are not critical, the reaction generally consumes reactants in the proportion of 1 mole of substituted styrene reactant to 1 or more moles of percarboxylic acid reactant. A suitable ratio of reactants is from about 1:1 to about 1:6 (substituted styrene:percarboxylic acid) and the employment of the reactants in a molar ratio of about 1:3 moles is preferred. The reaction is usually conducted at temperatures between about 20° and 120° C., preferably about 40° C., and is ordinarily carried out under ambient atmospheric pressure.

The resulting reaction mixture is usually maintained, with stirring, for a period of time sufficient to provide for substantial completion of the reaction. Generally the reaction is complete in a period of from about 1 hour to about 100 hours or more. Recovery of the desired product from the reaction mixture is achieved by employing conventional separatory and recovery procedures. Typically, the reaction mass is washed with water and neutralized with a sufficient amount of a base, e.g., sodium carbonate, bicarbonate, hydroxide or the like, and the desired product is recovered by concentration to dryness under reduced pressure.

Phenolic antioxidants are employed to reduce thermal decomposition of the peracid during epoxidation of the compounds of Formula II such as 4,4'-Thiobis(6-t-butyl-3-methyl-phenol), 2,6-Di-t-butyl-4-methylphenol, 4,4'-Butylidenebis-(6-t-butyl-3-methylphenol) and dilauryl 3,3'-thiodipropionate, preferably 4,4'-thiobis[6-tert-butyl-o-cresol.

Generally, yields of the oxirane propanamide compounds and of the olefinic amides in the examples which follow ranged from about 50 to about 90 percent. No attempts were made to optimize yields.

The following examples are presented to illustrate preparation of typical compounds employed in the invention, but the scope of the invention is not to be considered limited to the specific examples given.

EXAMPLE 1

α,α-Dichloro-2-(3,5-dichlorophenyl)oxiranepropanamide

About 10 grams (g) 2,2-dichloro-4-chloro-4-(3,5-dichlorophenyl)pentanoic acid chloride was diluted with 250 ml of benzene and sparged with anhydrous ammonia (NH$_3$) gas for several minutes until a strong odor of NH$_3$ persisted. The organic extract from the sparging was washed with water, dried over MgSO$_4$ and evaporated. The residue was diluted with 40 ml of 1,2-dichloroethane and 0.3 g of iron chloride (FeCl$_3$) was added and the solution was refluxed for 6 hours. After cooling, the reaction mixture was washed with dilute aqueous hydrochloric acid to remove the iron chloride. The product after washing was a dark viscous oil that could not be crystallized. The product was then purified by column chromatography using silica gel and eluting with methylene chloride to give the olefin.

Calculated for C$_{11}$H$_9$Cl$_4$ON: C, 42.20; H, 2.90; N, 4.47.

Analyzed: C, 43.3; H, 3.11; N, 4.52.

Two (2.0) g of the olefin prepared above was dissolved in 25 ml of 1,2-dichloroethane and 50 milligrams (mg) of Ethanox ® 736 was added thereto along with 3.0 g of m-chloroperbenzoic acid. After 90 minutes at reflux, the reaction was complete. m-Chlorobenzoic acid, a byproduct, was removed by washing the extract from the reaction with dilute NaHCO$_3$. The washed extract was dried over MgSO$_4$, filtered and the solvent evaporated off. Recrystallization of the residue with methylene chloride-hexane gave α,α-dichloro-2-(3,5-dichlorophenyl) -oxiranepropanamide. m.p. 130°–133° C.

Calculated for $C_{11}H_9NCl_4O_2$: C,40.15; H, 2.76; Cl, 43.10; N, 4.26.

Analyzed: C, 40.6; H 2.71; Cl, 43.8; N, 4.05.

EXAMPLE 2

N-(Aminocarbonyl)-α,α-dichloro-2-(3,5-dichlorophenyl)oxiranepropanamide

About 15 g of 2,2-dichloro-4-methylene-4-(3,5-dichlorophenyl)butanoic acid chloride was refluxed in 100 ml benzene for 12 hours with about 5 g finely powdered urea. The residue left, after evaporation of the benzene, was slurried in aqueous acetone and the insoluble fraction was filtered and dried to give the olefinic amide, m.p. 200°–203° C.

Calculated for $C_{12}H_{10}Cl_4N_2O_2$: C, 40.4; H, 2.80; Cl, 39.90; N, 7.86.

Analyzed: C, 40.64; H, 2.80; Cl, 40.5; N, 7.89.

Three (3.0) g of the olefinic amide prepared above was refluxed in 50 ml of 1,2-dichloroethane with 50 milligrams (mg) of Ethanox® 736 and 4.0 g of m-chloroperbenzoic acid for 3 hours. The refluxed mixture was poured into ethyl acetate and washed with dilute sodium sulfite and dilute sodium bicarbonate. After drying and evaporation of the solvent, the compound was recrystallized from ethyl acetate to give N-(aminocarbonyl)-α,α-dichloro-2-(3,5-dichlorophenyl)oxiranepropanamide, m.p. 186°–189° C.

Calculated for $C_{12}H_{10}Cl_4N_2O_3$: C, 38.70; H, 2.69; Cl, 38.12; N, 7.52.

Analyzed: C, 38.85; H, 2.73; Cl, 36.4; N, 7.49.

EXAMPLE 3

α,α-Dichloro-2-(3,5-dichlorophenyl)-N-(phenylmethyl)oxiranepropanamide

α,α-3,5-tetrachloro-o-methylene-N-(phenylmethyl)benzenebutanamide, m.p. 86°–89° C. was prepared from 3,5-dichloro-α-methylstyrene and trichloracetyl chloride using the procedures as set forth in Example 2, followed by dehydrochlorination and amination with benzylamine. The amide (2.21 g) and 3.0 g m-chloroperbenzoic acid was dissolved in 30 ml methylene chloride and stirred at room temperature for 48 hours. The methylene chloride mixture was washed with dilute sodium bisulfite and dilute sodium bicarbonate. After drying the methylene chloride mixture over sodium carbonate and evaporating off the solvent, the residue was recrystallized from 75 percent (%) ethanol to give α,α-2-dichloro-2-(3,5-dichlorophenyl)-N-(phenylmethyl)oxiranepropanamide, m.p. 115°–118° C. The nuclear magnetic resonance spectra for this compound was as follows: δ2.93 (q, 2, CH$_2$O), d 3.4 (s, 2, CH$_2$CCl$_2$), δ4.42 (d, 2, CH$_2$benzyl), 7.33 (m, 8, aromatic).

EXAMPLE 4

(2,2-Dichloro-3-[2-(3,5-dichlorophenyl)oxiranyl]-1-oxopropyl)carbamic acid, ethyl ester About 10 g of 2,2-dichloro-4-methylene-4-(3,5-dichlorophenyl)butanoic acid chloride and 20 g of ethyl urethane were heated together at 100° C. for 4 hours. After cooling, the product from the reaction was isolated by extraction. The extract was dried, heated to evaporate off the solvent and chromatographed on a column of silica gel. Elution of the column with benzene gave the olefinic carbamic acid ester, a viscous oil that could not be crystallized.

Calculated for $C_4H_{13}Cl_4NO_3$:, 43.67; H, 3.38; Cl, 36.84; N, 3.64.

Analyzed: C, 44.3; H, 3.24; Cl, 37.9; N, 3.50.

About 5 g of the olefinic carbamic acid ester, prepared hereinabove, was refluxed in 25 ml of 1,2-dichloroethane with 6 g of m-chloroperbenzoic acid and 50 mg of Ethanox® 736 for 2 hours. The product from the refluxed mixture was isolated by extraction using iodide ion to destroy excess peracid and dilute sodium sulfite for the iodine liberated. After washing the extracted product with sodium bicarbonate, drying and removal of the solvent, the residue was eluted on a column of silica gel with benzene:ethyl acetate (95:5 volume/volume). The eluted product, which could not be crystallized, was (2,2-dichloro-3-(2-(3,5-dichlorophenyl)oxiranyl)-1-oxopropyl)carbamic acid, ethyl ester.

Calculated for $C_{14}H_{13}Cl_4NO_3$: C, 41.93; H, 3.24; Cl, 35.37, N, 3.49.

Analyzed: C, 43.0; H, 2.99; Cl, 36.5; N, 2.40.

EXAMPLE 5

α,αDichloro-N-cyano-2-(3,5-dichlorophenyl)-N-(1-methylethyl)oxiranepropanamide

A benzene solution containing sodium isopropyl cyanamide was prepared by adding 4 g isopropyl cyanamide to a slight excess of sodium hydride to 100 ml benzene. About 10 g of 2,2-dichloro-4-methylene-4-(3,5-dichlorophenyl)butanoic acid chloride was added to this solution effecting an exothermic reaction. The product from the benzene solution was extracted with ethyl acetate, dried over MgSO$_4$ and recrystallized from benzene-hexane to give the olefinic N-cyanoamide, m.p. 126°–128° C.

Calculated for $C_{15}H_{14}Cl_4ON_2$: C, 47.39; H, 3.71; N, 7.36.

Analyzed: C, 47.4; H, 3.66; N, 7.31.

The olefinic N-cyanoamide (1.1 g) prepared above was refluxed in 50 ml of 1,2-dichloroethane along with 1.5 g of m-chloroperbenzoic acid and 50 mg of Ethanox® 736 for 3 hours. The product from the refluxed mixture was isolated by extraction and purified by column chromatography with silica gel to give α,α-dichloro-N-cyano-2(3,5-dichlorophenyl)-N-(1-methylethyl)oxiranepropanamide, a viscous oil.

Calculated for $C_{15}H_{14}Cl_4O_2N_2$: C, 45.5; H, 3.56; N, 7.06.

Analyzed: C, 45.6; H, 3.58; N, 6.95.

EXAMPLE 6

(α,α-Dichloro-2-(3,5-dichlorophenyl)-N-(2,6-diethylphenyl)oxiranepropanamide

Three grams of 2,2-dichloro-4-methylene-(3,5-dichlorophenyl)butanoic acid chloride was diluted with 25 ml of benzene. The benzene solution was added dropwise at room temperature over a 1 hour period to a solution containing 3.0 g of 2,6-diethylaniline and 2.0 g of triethylamine in 50 ml of benzene. The product from the combined benzene solutions was isolated by extraction and recrystallized from benzene to give the olefinic amide, m.p. 156°–158° C.

Calculated for $C_{21}H_{20}Cl_4NO$: C, 56.65; H, 4.75; Cl, 31.85; N, 3.14;

Analyzed: C, 56.7; H, 4.66; Cl, 32.6; N, 3.06.

The olefinic amide (2.0 g), prepared above, and 2.0 g of m-chloroperbenzoic acid were refluxed for 2 hours in 50 ml of 1,2-dichloroethane along with 50 mg Ethanox® 736. Excess m-chloroperbenzoic acid was neutralized with excess $Na_2SO_3$ using iodide ion as an indicator. The product from the refluxed mixture was washed with dilute sodium bicarbonate and dried over $MgSO_4$. Evaporation of the solvent and recrystallization of the residue from benzene-hexane gave α,α-2-dichloro-2-(3,5-dichlorophenyl)-N-2,6-(diethylphenyl)oxiranepropanamide, m.p. 150°–153° C.

Calculated for $C_{21}H_{21}Cl_4NO_2$: C, 54.69; H, 4.59; Cl, 30.75; N, 3.03.

Analyzed: C, 54.60; H, 4.47; Cl, 30.3; N, 3.00.

EXAMPLE 7

α,α-Dichloro-2-(3,5-dichlorophenyl)-N-methyl-N-((methylamino)carbonyl)oxiranepropanamide About 14 g of 2,2-dichloro-4-methylene-4-(3,5-dichlorophenyl)butanoic acid chloride and 8.8 g of dimethylurea were refluxed in 400 ml of benzene for 2 hours. The refluxed mixture was washed with water, dried over $MgSO_4$ and filtered with benzene through aluminum oxide (80–200 mesh, acid, Brockman Grade 1). Evaporation of the benzene gave the olefinic urea, as a viscous oil. Infrared and nuclear magnetic resonance analyses were in agreement for the structure of this compound.

The olefinic urea (5 g), as prepared above, 5 g of m-chloroperbenzoic acid and 50 mg of Ethanox® 736 were refluxed for 2 hours in 50 ml of 1,2-dichloroethane. Excess peracid was removed by washing the organic extract with sodium sulfite and then with sodium bicarbonate solutions. After drying, the product was purified by column chromatography on alumina oxide (basic, Brockman Grade 1) to give α,α-2-dichloro-2-(3,5-dichlorophenyl)-N-methyl-N-((methylamino)carbonyl)oxiranepropanamide, a viscous oil.

Calculated for $C_{14}H_{13}N_2Cl_4O_3$: C, 42.13; H, 3.28; Cl, 35.5; N, 7.02.

Analyzed: C, 43.10; H, 3.46; Cl, 35.0; N, 6.64.

EXAMPLE 8

α,α-Dichloro-2-(3,5-dichlorophenyl)-N-(1,1-dimethylethyl)oxiranepropanamide

About 10 g of 2,2-dichloro-4-methylene-(3,5-dichlorophenyl)butanoic acid chloride was dissolved in 50 ml benzene. Then 2.19 g of t-butylamine in 5 ml of pyridine was added dropwise at room temperature to the benzene solution. After the addition was complete, the combined solutions were stirred for an additional 30 minutes. The combined solutions were further diluted with benzene, washed several times with water, dried over $MgSO_4$ and the solvent evaporated off to give the olefinic amide, a viscous oil.

Calculated for $C_{15}H_{17}Cl_4NO$: C, 48.80; H, 4.61; Cl, 38.45, N, 3.80.

Analyzed: C, 49.1; H, 4.55, Cl, 37.80; N, 3.60.

The olefinic amide (2 g), prepared above, and 2.0 g of m-chloroperbenzoic acid were stirred at room temperature for 60 hours. The product isolated from the stirred mixture by extraction, drying and evaporation was α,α-2-dichloro-2-(3,5-dichlorophenyl)-N-(1,1-dimethylethyl)oxiranepropanamide, a viscous oil. Nuclear magnetic resonance and infrared analysis showed the oil to be a mixture of the desired oxiranepropionamide (65%) and a previously characterized lactone (35%).

EXAMPLE 9

2-(3,5-Dichlorophenyl)-α,-60-difluoroxiranepropanamide

About 20 g of 3,5-dichloro-α-methylstyrene and 50 g ethylbromodifluoroacetate were heated at 150° C. in a Parr Bomb along with 2 g cuprous chloride and 2 g triphenylphosphine for 16 hours. The crude product from the heated mixture was chromatographed on silica gel, (80–200 mesh) eluted with benzene:ethyl acetate (95:5 volume/volume) and recrystallized from methylene chloride-hexane to give the olefinic amide, m.p. 92°–94° C.

Calculated for $C_{11}H_9Cl_2F_2NO$: C, 47.16; H, 3.24; Cl, 25.3; N, 5.0.

Analyzed: C, 47.20; H, 3.29; Cl, 24.9; N, 4.92.

The olefinic amide (1 g), prepared above, and 1.5 g of m-chloroperbenzoic acid were stirred in 25 ml of methylene chloride for 48 hours. After stirring, the methylene chloride solution was washed with sodium sulfite and sodium bicarbonate, dried over $MgSO_4$, evaporated and the residue recrystallized from $CH_2Cl_2$-hexane to give 2,2-difluoro-2-(3,5-dichlorophenyl)oxiranepropionamide, m.p. 90°–92° C.

Calculated for $C_{13}H_{16}Cl_2F_2NO_2$: C, 44.69; H, 3.06; Cl, 23.76; N, 4.74.

Analyzed: C, 44,50; H, 3.02; Cl, 24.40; N, 4.60.

EXAMPLE 10

α,α-Dichloro-2-(3-chlorophenyl)oxiranepropanamide

About 9.16 g of 3-chloro-α-methylstyrene containing 0.1 g of triphenylphosphine was added dropwise to a refluxing solution of trichloroacetyl chloride containing 0.1 g of cuprous chloride. After 1 hour the refluxed mixture was cooled, filtered, and the excess trichloroacetyl chloride removed with a Buchler evaporator to give the crude acid chloride. The crude acid chloride was diluted with 100 ml carbon tetrachloride, to which 2.5 g alumina was added. The carbon tetrachloride mixture was refluxed for 29 hours, after which the olefin formation was complete. The alumina catalyst was removed by filtration and the filtrate was treated with anhydrous ammonia. Washing, drying, removal of the solvent and distillation on a Kugelrohr at 120° C. at 0.5 mm Hg gave the olefinic amide. The nuclear magnetic resonance for this compound was as follows: ($CDCl_3$): δ6 3.64 (d, 2, $CH_2$), δ5.50 (d, 2, olefinic $CH_2$), δ6.77 (broad, 2, $NH_2$); δ6, 7.33 (m, 4, aromatic).

The olefinic amide (4.10 g) was dissolved in 20 ml methylene chloride to which 4.0 g of m-chloroperbenzoic acid was added. The methylene chloride solution was stirred for 60 hours along with powdered sodium carbonate. The methylene chloride solution was washed with sodium bisulfite and sodium bicarbonate and the solvent evaporated to give α,α-2-dichloro-2-(3-chlorophenyl)oxiranepropanamide, a light yellow oil.

The nuclear magnetic resonance spectra for this compound was as follows: δ2.88 (q, 2, $CH_2$—O), δ 3.26 (s, 2, $CH_2$), δ6.77 (b, 2, $NH_2$), 67 7.25 (m, 4, aromatic).

EXAMPLE 11

α,α-Dichloro-N-(phenylmethyl)-2-(3-trifluoromethyl)-phenyl)oxiranepropanamide

α,α-Dichloro-α-methylene-N-phenylmethyl)-3(trifluoro)benzenebutanamide was prepared by the addition of trichloroacetyl chloride to 3-trifluoromethyl-α- methylstyrene, followed by dehydrochlorination and amination to give the olefinic amide, m.p. 48.5°–52° C. The olefinic amide (1.11 g) and 0.96 g of m-chloroperbenzoic acid was dissolved in 30 ml methylene chloride and stirred at room temperature for 48 hours. The methylene chloride mixture was washed with dilute sodium bisulfite and dilute sodium bicarbonate and dried over potassium carbonate. Evaporation of the solvent gave α,α-dichloro-N-(phenylmethyl)-2-(3-trifluoromethyl)-phenyl)oxiranepropanamide, a yellow oil which crystallized on standing. The crystals were slurried in hexane, filtered and dried, m.p. 75°–80° C. The nuclear magnetic resonance spectra for this compound was as follows: δ 2.88 (q, 2, $CH_2O$), δ 2.40 (d, 2, $CH_2CCl_2$), δ 4.28 (d, 2, $CH_2benzyl$), δ 7.50 (m, 9, aromatic).

Preparation of Starting Materials

Generally, the novel substituted styrene compounds of Formula II may be prepared by the steps of:

(A) reacting an appropriate substituted α-methylstyrene with an aliphatic polyhalogen acid derivative to form an aromatic polyhalogen acid derivative; and (B) reacting the aromatic polyhalogen acid derivative with a solution containing benzene and an appropriate amine ($HNR^1R^2$), followed by dehydrohalogenation with a Lewis Acid, preferably iron chloride ($FeCl_3$) in an inert organic solvent, preferably 1,2-dichloroethane (EDC) to give the substituted styrene (an olefinic amide). In an alternative procedure, the aromatic polyhalogen acid derivative is dehydrohalogenated with the Lewis Acid, followed by reaction with the appropriate amine under conditions described hereinbelow. The reactions can be schematically illustrated as follows:

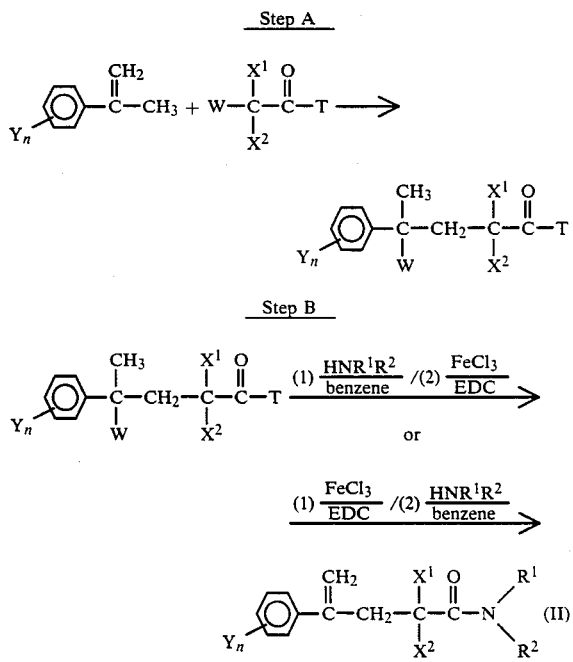

wherein Y, n, $X^1$ and $X^2$ are as previously defined. W, T and $HNR^1R^2$ are as defined hereinbelow.

In carrying out the reaction for Step A, the substituted α-methyl styrene is reacted with the aliphatic polyhalogen acid derivative in the presence of a transition metal salt, such as copper(II) oxide, iron(III) oxide: Cu(I)-, Cu(II)-, Fe(II)- and Fe(III)-bromides and -iodides and particularly -chlorides, zinc chloride, as well as the chlorides of ruthenium, of rhodium, of palladium, of cobalt and of nickel; Cu(II)-sulfate, Fe(II)-and Fe(III)-sulfate, Cu(II) nitrate and iron(III) nitrate; manganese(III) acetate, copper(II) acetate, copper(II) stearate, iron(III) citrate, Cu(I)-cyanide; ruthenium(II) dichloro-tris-triphenylphosphine, rhodium-dichloro-tris-triphenylphosphine; chromium and nickel-acetylacetonate, copper(II) acetylacetonate, iron(III) acetylacetonate, cobalt(II)- and cobalt(III)- acetylacetonate, manganese(II) acetylacetonate, copper(II)-benzoylacetonate; iron carbonyl-cyclopentadienyl complex; molybdenum carbonylcyclopentadienyl complex, chromium-tricarbonylaryl complexes, ruthenium(II) acetate complex, chromium- and molybdenumhexacarbonyl, nickel tetracarbonyl, iron pentacarbonyl and cobalt- and manganese-carbonyl, preferably cuprous chloride (CuCl), as disclosed in U.S. Pat. No. 4,327,216.

The reaction for Step A is conducted with or without amine co-catalysts such as triethylamine and tributylamine, or phosphine co-catalysts such as triphenyl phosphine and tributylphosphine, which do not react appreciably with either the substituted α-methylstyrene nor with the aliphatic polyhalogen acid derivative. While the amounts of the reactants to be employed are not critical, the reaction generally consumes reactants in the proportion of 1 mole of substituted α-methyl styrene reactant to 1 or more moles of the aliphatic polyhalogen acid derivative. A suitable ratio of reactants is from about 1:1 to about 1:5 (substituted α-methyl styrene:aliphatic polyhalogen acid derivative), preferably about 1:2. The reaction is usually conducted at temperatures between about 40° and 180° C. and is ordinarily carried out under ambient pressure, although pressures greater than ambient can be employed. The resulting reaction mixture is usually maintained, with stirring, for a period of time sufficient to provide for substantial completion of the reaction. Generally, the reaction is completed in a period of about 1 to about 48 hours or more. Recovery of the desired aromatic polyhalogen acid derivative from the reaction mixture is achieved by employing conventional separatory and recovery procedures, such as precipitation, extraction, chromatography, and crystallization.

The reactions for Step B are usually carried out by mixing the aromatic polyhalogen acid derivative formed in Step A in a reaction medium, such as, for example, benzene, with an appropriate amine. A suitable molar ratio of reactants is from about 1:2.5 to about 1:5 (aromatic polyhalogen acid derivative:appropriate amine), usually with a slight excess of the amine. Generally, the reaction is stirred for a period of about 1 to about 6 hours or more. The reaction is usually conducted at ambient temperatures and is ordinarily carried out under ambient atmospheric pressure. Recovery of the desired amine product from the reaction mixture is achieved by employing conventional separation and recovery procedures such as precipitation, extraction, chromatography, crystallization, and the like.

Following treatment with the appropriate amine, the reactions of Step B are completed by mixing the hereinabove amine product with a suitable organic solvent such as 1,2-dichloroethane, carbon tetrachloride, chloroform, 1,2-dichloroethane, methyl chloroform, tetrachloroethylene, trichloroethylene or chlorobenzene, and a catalytic amount of alumina or a Lewis Acid such as $FeCl_3$, zinc chloride ($ZnCl_2$), boron trifluoride ($BF_3$)

or aluminum chloride (AlCl₃), preferably from about 0.5 to about 3 percent Lewis Acid, more preferably 1 percent. Generally, the reaction is stirred for a period of about 1 to about 12 hours or more. The reaction is usually conducted under reflux temperatures and is ordinarily carried out under ambient atmospheric pressure. Recovery of the desired substituted styrenes of Formula II from the reaction mixture is achieved by employing conventional separatory and recovery procedures, such as those employed hereinabove in similar Step B processes.

Suitable aliphatic polyhalogen acid derivatives of the formula:

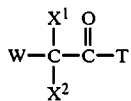

wherein $X^1$ and $X^2$ are as previously defined; W is chlorine, bromine or iodine; and T is an acid derivative such as carboxylic acid halide, amide or ester are well-known compounds.

Generally, the polyhalogen acid halide derivative may be formed by reacting a polyhalogen acid ($WCX^1X^2COOH$) with any of the following: thionyl chloride, phosgene or oxalyl halide, preferably oxalyl chloride. The corresponding polyhalogen esters and amide derivatives are formed by reaction of the polyhalogen acid halide with alcohols or amines, respectively. The reaction conditions for making the derivatives are known to those of ordinary skill in the art.

Appropriate amines for reacting with the aromatic polyhalogen acid halide to give the olefinic amide are of the formula:

wherein $R^1$ and $R^2$ each can be
hydrogen,
cyano,
loweralkyl,
cycloalkyl,
aryl,
aralkyl,
—COOR (wherein R represents hydrogen or lower alkyl) or
—$CONZ^1Z^2$ wherein $Z^1$ and $Z^2$ independently represent
hydrogen,
cyano,
loweralkyl,
cycloalkyl,
aryl or
aralkyl.
The hereinabove amines are all known compounds readily available to those skilled in the art.

The substituted α-methylstyrene compounds employed as starting materials are all known compounds and can be prepared in accordance with known or analogous methods such as those taught in U.S. Pat. Nos. 3,391,203 and 3,336,401 which are incorporated herein by reference.

EXAMPLE 12

2,2-Dichloro-4-methylene-4-(3,5-dichlorophenyl)-butanoic acid amide

About 92 g of trichloroacetyl chloride (0.5 mole) and 1 g cuprous chloride were placed into a three-necked 250 ml flask equipped with a magnetic stirrer, a thermometer, a dropping funnel and a reflux condenser and heated to reflux. About 0.2 moles of 3,5-dichloro-α-methylstyrene containing 1 g triphenylphosphine was added dropwise over a 1 hour period. The mixture was refluxed an additional 30 minutes and cooled. Nuclear magnetic resonance analysis of the mixture showed the disappearance of 3,5-dichloro-α-methylstyrene and the formation of the aromatic polyhalogen acid chloride, 2,2-dichloro-4-methylene-4-(3,5-dichlorophenyl)-butanoic acid chloride. The excess trichloroacetyl chloride in the refluxed mixture was removed with a Buchler evaporator and the mixture was filtered to remove the cuprous chloride and triphenylphosphine catalyst.

The filtrate was diluted with 300 ml of 1,2-dichloroethane and refluxed for three hours along with 5 g powdered either anhydrous zinc chloride or 1 g FeCl₃. After reflux, the reaction mixture was cooled, filtered and the solvent evaporated off. The residue was slurried in hexane, filtered again to remove residual catalysts and evaporated on a Buchler to give the aromatic polyhalogen acid halide, 2,2-dichloro-4-methylene-4-(3,5-dichlorophenyl)butanoic acid chloride. This compound was used to prepare the olefinic amide without further purification.

The nuclear magnetic resonance for this compound in CDCl₃ was as follows: δ 3.60 (S, 2, CH₂); δ 5.50 (d, 2, exo methylene); δ 7.25 (m, 3, aromatic).

About 10 grams (g) 2,2-dichloro-4-chloro-4-(3,5-dichlorophenyl)pentanoic acid chloride was diluted with 250 ml of benzene and sparged with anyhdrous ammonia (NH₃) gas for several minutes until a strong odor of NH₃ persisted. The organic extract from the sparging was washed with water, dried over MgSO₄ and evaporated. The residue left after evaporation was diluted with 40 ml of 1,2-dichloroethane, 0.3 g of iron chloride (FeCl₃) was added and the organic solution of the residue, the 1,2-dichloroethane, and the FeCl₃ was refluxed for 6 hours. After cooling, the organic solution was washed with dilute aqueous hydrochloric acid to remove the iron chloride. The product after washing was a dark viscous oil that could not be crystallized. The product was then purified by column chromatography using silica gel and eluting with methylene chloride to give the olefinic amide, 2,2-dichloro-4-methylene-4-(3,5-dichlorophenyl)butanoic acid amide.

Calculated for C₁₁H₉Cl₄ON: C, 42.20; H, 2.90; N, 4.47.

Analyzed: C, 43.30; H, 3.11; N, 4.42

As indicated hereinbefore, the compounds of the present invention are useful as herbicides. The growth inhibition, or herbicidal activity of these compounds may be demonstrated by contacting a plant structure with the subject compounds, which may take place either preemergently or postemergently to established plants. Preemergence application may be accomplished by application of the compounds to the surface of the soil or by incorporation of the compounds into the surface layer of soil.

In particular, it has been discovered that undesirable plants can be controlled by contacting such plants and/or their habitats with compositions containing an effective growth-controlling amount of at least one of the oxirane compounds disclosed herein. When the germinant seeds and emerging seedlings of many terrestrial plant species are contacted with compositions containing one or more of the oxirane compounds in dosages sufficient to supply from about 1.0 to about 50.0 pounds (lb) of the compound per acre, an acceptable inhibition of the growth of such seeds and seedlings can be obtained.

Not all the compounds of the present invention are equally effective in selectively killing and controlling undesirable weed species in the presence of the desired crop. For example, some compounds are more effective when applied preemergent rather than when applied postemergent. Some compounds will control both broadleaf and grassy weeds while others will control primarily grassy weeds. When applied to the same weed species, some compounds are more effective at a lower dosage rate than are other compounds. Also, some of the oxirane compounds of the present invention will provide selective weed control for a greater number of desired crop species than other of the oxirane compounds.

Compositions employing certain of the oxirane compounds at dosages of from about 250 to about 4,000 or more parts by weight per million parts of ultimate treating composition are effective in controlling the growth of the established plants of several plant species. In many instances, the application of the compositions containing certain oxirane compounds in dosages of from about 250 to about 1000 parts per million by weight per million parts of treating composition results in the selective postemergent control of many undesirable plant species, especially those of small-seeded grasses in areas supporting the growth of the established plants of desired crops, e.g., corn, cultured rice and white winter wheat, particularly cotton. In all selective operations, the exact dosage to be employed is dependent upon the resistance of the crop plants to the particular oxirane composition employed and other related factors more fully explained hereinafter.

The application to plants, plant-parts, rooting zones and/or their habitats of a composition containing a growth-suppressing amount of an oxirane compound is essential and critical for the practice of the present invention. The exact dosage to be supplied by the composition in a given operation is dependent upon the plant species and upon the stage of growth and hardiness thereof as well as upon the plant part to be exposed to the pesticidal composition. Other factors, such as, for example, weather, bacteria and other organisms found in the soil must also be considered. Thus, while the application of low amounts of active compounds per acre may be sufficient for good control of a light infestation of weeds growing under adverse conditions, applications of from 5 to 20 pounds or more of active compound per acre may be required for good control of a dense infestation of hardy weeds growing under favorable growth conditions.

Compositions comprising an oxirane compound with an inert material known as an agricultural adjuvant or carrier in solid or liquid form allow the growth-suppressing amount of the active ingredient to be mixed in such quantity of ultimate treating material that adequate coverage of all plants and plant-parts or adequate admixture with their habitats (e.g., soil) can be obtained. An adjuvant is defined herein as any substance in a herbicide formulation or added to the formulation to improve herbicidal activity or application characteristics. Good growth-suppressing results are obtained when employing a carrier material in relatively small, but effective amounts. Generally, however, the best results are obtained by employing either a surface-active dispersing agent, in an amount sufficient to emulsify the oxirane compound with an organic solvent or with water as a carrier, for example, an amount which represents from 0.1 to 15 percent, by weight, of the total treating material; or a finely divided carrier solid, in an amount which represents from about 40 to about 99.5 percent, by weight, of the total treating material.

The exact concentration of the oxirane compounds employed in the compositions for application to plants, plant-parts and/or their habitats is not critical and can vary considerably provided the required dosage of effective agent is supplied to the plant, plant-part, rooting zone, and/or habitat treated. The concentration of the oxirane compound in liquid compositions employed to supply the desired dosage generally is from about 0.01 to about 50 percent by weight, although concentrations as high as 90 percent by weight are sometimes conveniently employed. In finely divided solid carrier compositions, the concentration of the oxirane compound can be from 0.1 to 60 percent by weight. In compositions to be employed as concentrates, the oxirane compound can be present in a concentration of from about 5 to about 98 percent by weight.

In preemergent operations for selective uses a dosage of about 0.1 to about 20 lb/acre or more is generally applicable, a rate of 0.5 to 10 lb/acre being preferred.

In postemergent operations, a dosage of about 0.01 to about 20 pounds/acre or more is generally applicable. A dosage rate in the range of about 0.5 to about 8 lb/acre is preferred.

The quantity of treating compositions to be applied can vary considerably provided that the required dosage of active ingredient is applied in sufficient of the finished composition to facilitate the distribution of the active agent on the plant or plant-part, or the penetration of the active ingredient into the plant habitat. The required amount of the active agent conveniently can be supplied per acre treated in from about 10 to 27,000 gallons or more of the liquid carrier or in from about 10 to 2,000 pounds of the finely divided solid carrier.

Liquid compositions employed as a spray containing the desired amount of active ingredient can be prepared by dissolving the oxirane compound in an organic liquid carrier or by dispersing the oxirane compound in water with or without the aid of a suitable surface-active dispersing agent such as an ionic or non-ionic emulsifying agent. Suitable organic liquid carriers include the agricultural spray oils and the petroleum distillates such as diesel fuel, kerosene, fuel oil naphthas and Stoddard solvent. Among the organic liquid carriers, the petroleum distillates are generally preferred. The aqueous compositions can contain one or more water immiscible solvents for the oxirane compound. In such compositions, the carrier comprises an aqueous emulsion, i.e., a mixture of water, emulsifying agent and water immiscible solvent. The choice of dispersing and emulsifying agent and the amount thereof employed is dictated by the nature of the composition and by the ability of the agent to facilitate the dispersion of the oxirane compound in the carrier to produce the desired composition. Dispersing and emulsifying agents which can be employed in the compositions include the condensation products of alkylene oxides with phenols and organic acids, alkyl aryl sulfonates, polyoxyalkylene derivatives of sorbitan esters, complex ether alcohols, mahogany soaps, and the like.

In the preparation of dust compositions, the active ingredient is dispersed in and on a finely divided solid carrier such as clay, talc, chalk, gypsum, bentonite, fuller's earth, attapulgite, and the like. In such operation, the finely divided carrier is mechanically mixed or ground with the oxirane compound. Depending upon the proportion of ingredients, these dust compositions can be employed as concentrates and subsequently diluted with additional solid carrier or with liquid or solid surface-active dispersing agent to obtain the desired amount of active ingredient in a composition adapted to be employed for the suppression of the growth of the plants. Also, such dust compositions, particularly when finely ground or milled, can be dispersed in water, preferably with the aid of a surface-active dispersing agent, to form spray mixtures.

Suitable adjuvants useful in making up compositions of the foregoing type are well known to those skilled in the art. The methods of applying the solid or liquid herbicidal formulations similarly are well known to the skilled artisan.

Satisfactory results are obtained when the oxirane compositions are combined with other agricultural materials intended to be applied to plants, plant-parts and/or their habitats. Such materials include fertilizers, fungicides, insecticides, acaricides, nematocides, bactericides, soil conditioning agents, other herbicides, usually with a complementary spectrum of weed control, and the like.

When operating in accordance with the present invention, compositions containing growth-suppressing amounts of the oxirane compounds re applied to plants, plant-parts and/or their habitats in any convenient fashion. Applications to a plant habitat, e.g., soil, can be carried out by simply mixing with the habitat, such as by applying to the surface of soil by spraying a liquid composition and thereafter dragging or discing into the soil to the desired depth or by employing a liquid carrier to accomplish the penetration and impregnation. The application of spray and dust compositions to the surface of soil can be carried out by conventional methods, e.g., power dusters, boom and hand sprayers and spray dusters.

In a further method, the distribution of the oxirane compositions in soil can be accomplished by introducing the active ingredient in the water employed to irrigate the soil. In such procedures, the amount of water can be varied with the porosity and water holding capacity of the soil to obtain a desired depth of distribution of the agent.

In addition, the present method also comprehends the employment of an aerosol composition containing an oxirane compound as an active compound. Such a composition is prepared according to conventional methods wherein the active ingredient is dispersed in a solvent, and the resultant dispersion mixed with a readily volatilized liquid propellant. Such variables as the particular active ingredient to be used and the particular plant part to be treated will determine the identity of the solvent and the concentration of the active ingredient therein. Examples of suitable solvents are water, acetone, isopropanol, and 2-ethoxyethanol. Also, employment of the oxirane compound in pastes, gels, foams, invert emulsions, and the like, as well as pigmented or unpigmented pelleted solids is comprehended.

The following examples further illustrate the present invention.

EXAMPLE 12

Preemergence Operations

Representative compositions of the present invention were evaluated for the preemergent control of various plant species.

Each compound tested was dissolved in acetone to one half of the final volume used (twice the final concentration) and the acetone solution in each case was admixed with an equal volume of water containing 0.1 percent by weight of Tween-20 surface active material (Tween-20 is a trademark of Atlas Chemical Company). The composition, generally in the nature of an emulsion, was employed to treat separate respective seed beds of sandy loam soil of good nutrient content wherein each seed bed contained separate groups of good viable seeds, each group being of one of a known plant species. The various beds were positioned side by side and exposed to substantially identical conditions of temperature and light. Each bed was maintained so as to prevent any interaction with the test compound in different seeds beds. Each seed bed was treated with the composition as a spray employing conventional spraying equipment to deposit a predetermined amount of the compound uniformly throughout the surface of the bed at a rate of about 10 pounds per acre. Another seed bed was treated only with the acetone-Tween-20 water mixture with no chemical added to serve as checks. After treatment, the seed beds were maintained for two weeks under greenhouse conditions conducive for good plant growth and watered as necessary. "Control" refers to the reduction in growth of the test species in the presence of the test chemical relative to the observed growth of the same species in the absence of the test chemical. Two weeks after treatment, the beds were examined for plant growth and evaluated. The specific plant species and the percent kill and control obtained are set forth in Table 1.

TABLE 1

| PREEMERGENT KILL AND CONTROL OF SEED GERMINATION | | | | | | |
|---|---|---|---|---|---|---|
| Compound Tested | Pigweed | Crabgrass | Barnyard Grass | Wild Oats | Yellow Foxtail | Cotton |
| | Percent Kill and Control[1] | | | | | |
| α,α-dichloro-2-(3,5-dichlorophenyl)oxiranepropanamide | 100 | 100 | — | 100 | 100 | 0 |
| α,α-dichloro-2-(3,5-dichlorophenyl)-N-(1,1-dimethylethyl)-oxiranepropanamide | 100 | 100 | 100 | 90 | 100 | 0 |
| 2-(3,5-dichlorophenyl)-α,α-di- | | | | | | |

TABLE 1-continued

PREEMERGENT KILL AND CONTROL OF SEED GERMINATION

| Compound Tested | Pigweed | Crabgrass | Barnyard Grass | Wild Oats | Yellow Foxtail | Cotton |
|---|---|---|---|---|---|---|
| fluorooxiranepropanamide | 0 | 100 | 100 | 100 | 100 | 0 |
| N-(aminocarbonyl)-α,α-dichloro-2-(3,5-dichlorophenyl)oxiranepropanamide | 0 | 40 | 30 | 0 | 40 | 0 |
| α,α-dichloro-2-(3,5-dichlorophenyl)-N-methyl-N-((methylamino)carbonyl)oxiranepropanamide | 30 | 100 | 95 | 80 | 90 | 0 |
| α,α-dichloro-2-(3,5-dichlorophenyl)-N-(2,6-diethylphenyl)-oxiranepropanamide | 0 | 0 | 100 | 0 | — | 0 |

[1]Percent Kill and Control evaluated on a scale of 0 to 100. A percent control of "0" indicates there were no visible effects. A "100" indicates all plants were dead.
"—" indicates this treatment was not tested.

EXAMPLE 13

Preemergence Operations

In further representative preemergence operations similar to those set forth in Example 12, α,α-dichloro-2-(3,5-dichlorophenyl)-N-(phenylmethyl)oxiranepropanamide was found to give substantially complete kill and control of Johnson grass, wild oats and yellow foxtail at dosage rates of about one pound per acre while causing little or no damage to cotton, soybeans, corn, rape, cultivated rice or sugarbeets at the same dosage. Similarily, α,α-dichloro-N-(phenylmethyl)-2-(3-trifluoromethylphenyl)oxiranepropanamide was found to give satisfactory kill and control of barnyard grass and good control of wild oats at a dosage rate of about two pounds per acre while causing little or no damage to cotton, corn, white winter wheat, rape, cultivated rice or sugarbeets at the same dosage.

EXAMPLE 14

Postemergence Operations

Representative compositions of the present invention were evaluated for the postemergence control of various plant species. In these evaluations, plots of known plant species were grown to a height of about 4 inches. Aqueous spray compositions, containing oxirane compounds in a concentration of 4000 ppm was applied to separate plots. This concentration corresponds to a concentration of approximately 8 pounds active ingredient per acre. The spray compositions were made by mixing the active ingredient in acetone. An equal amount of water was added to the active ingredient/acetone mixture wherein the water contained 0.1 percent by weight of TWEEN ® 20 surfactant. The application to the plants was made to the point of run-off and was carried out with conventional spraying equipment. Other plots were sprayed with similar compositions containing no toxicant to serve as checks. Thereafter, the plots were maintained under conditions conducive for plant growth. Two weeks after treatment, the plots were examined for plant growth and evaluated. The results of the examination of the treated plots are set forth below in Table 2.

TABLE II

POSTEMERGENT KILL AND CONTROL OF PLANT SPECIES

| Compound Tested | Nutsedge | Pigweed | Crabgrass | Barnyard Grass | Yellow Foxtail | Cotton |
|---|---|---|---|---|---|---|
| (2,2-dichloro-3-(2-(3,5-dichlorophenyl)oxiranyl)-1-oxopropyl)carbamic acid, ethyl ester | 100 | 40 | 99 | 40 | 95 | — |
| α,α-dichloro-2-(3,5-dichlorophenyl)-N-methyl-N-((methylamino)carbonyl)oxiranepropanamide | 0 | 100 | 100 | 70 | 75 | 0 |
| 2-(3,5-chlorophenyl)-α,α-difluorooxiranepropanamide | 90 | 0 | 98 | 40 | 98 | 20 |

[1]Percent Control evaluated on a scale of 0 to 100. A percent control of "0" indicates there were no visible effects. A "100" indicates all plants were dead.
"—" indicates this treatment was not tested.

In further representative postemergent operations, α,α-dichloro-N-cyano-2-(3,5-dichlorophenyl)-N-1-methylethyl)-oxiranepropanamide was found to give very good kill and control of morning glory at dosage rate of 4000 ppm.

Substantially the same fine results are obtained upon applying other compounds of the present invention to undesirable plant species according to the procedures hereinbefore described.

What is claimed is:

1. A compound of the formula

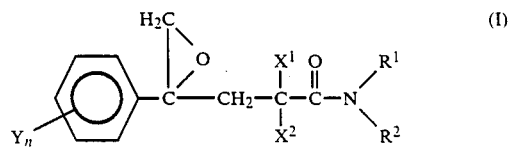

(I)

wherein
Y represents halogen, —CF₃ or methyl;
n represents an integer from 1 to 5, inclusive;
X¹ and X² independently represent chlorine, fluorine, bromine or iodine; and
R¹ and R² independently represent
hydrogen,
cyano,
loweralkyl,
cycloalkyl,
aryl,
aralkyl,
—COOR wherein R represents hydrogen or loweralkyl or
—CONZ¹Z² wherein
Z¹ and Z² independently represent
hydrogen,
cyano,
loweralkyl,
cycloalkyl,
aryl or
aralkyl.

2. The compound according to claim 1 which is α,α-dichloro-2-(3,5-dichlorophenyl)oxiranepropanamide.

3. The compound according to claim 1 which is α,α-dichloro-2-(3,5-dichlorophenyl)-N-(1,1-dimethylethyl)oxiranepropanamide.

4. The compound according to claim 1 which is 2-(3,5-dichlorophenyl)-α,α-difluorooxiranepropanamide.

5. The compound according to claim 1 which is α,α-dichloro-2-(3-chlorophenyl)oxiranepropanamide.

6. The compound according to claim 1 which is α,α-dichloro-N-(phenylmethyl)-2-(3-(trifluoromethyl)phenyl)oxiranepropanamide.

7. A composition comprising an inert carrier and a herbicidally-effective amount of a compound, as the active material, corresponds to the formula

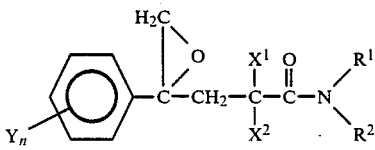

wherein
Y represents halogen, —CF₃ or methyl;
n represents an integer from 1 to 5, inclusive;
X¹ and X² independently represent chlorine, fluorine, bromine or iodine; and
R¹ and R² independently represent
hydrogen,
cyano,
loweralkyl,
cycloalkyl,
aryl,
aralkyl,
—COOR wherein R represents hydrogen or loweralkyl or
—CONZ¹Z² wherein Z¹ and Z² independently represent
hydrogen,
cyano,
loweralkyl,
cycloalkyl,
aryl or
aralkyl.

8. The composition according to claim 7 wherein the active material is α,α-dichloro-2-(3,5-dichlorophenyl)oxiranepropanamide.

9. The composition according to claim 7 wherein the active material is α,α-dichloro-2-(3,5-dichlorophenyl)-N-(1,1-dimethylethyl)-oxiranepropanamide.

10. The composition according to claim 7 wherein the active material is 2-(3,5-dichlorophenyl)-α,α-difluorooxiranepropanamide.

11. The composition according to claim 7 wherein the active material is α,α-dichloro-2-(3-chlorophenyl)oxiranepropanamide.

12. The composition according to claim 7 wherein the active material is α,α-dichloro-N-(phenylmethyl)-2-(3-(trifluoromethyl)phenyl)oxiranepropanamide.

13. A method for controlling undesirable plants which comprises applying to the locus of said plants a herbicidally effective amount of a composition comprising an inert carrier in intimate admixture with, as the active material, a substituted oxirane compound corresponding to the formula

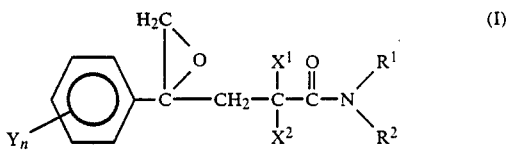

wherein
Y represents halogen, —CF₃ or methyl;
n represents an integer from 1 to 5, inclusive;
X¹ and X² independently represent chlorine, fluorine, bromine or iodine; and
R¹ and R² independently represent
hydrogen,
cyano,
loweralkyl,
cycloalkyl,
aryl,
aralkyl,
—COOR wherein R represents hydrogen or loweralkyl, and
—CONZ¹Z² wherein Z¹ and Z² independently represent
hydrogen,
cyano,
loweralkyl,
cycloalkyl,
aryl or
aralkyl.

14. The method according to claim 13 wherein the active material is α,α-dichloro-2-(3,5-dichlorophenyl)-oxiranepropanamide.

15. The method according to claim 13 wherein the active material is α,α-dichloro-2-(3,5-dichlorophenyl)-N-(1,1-dimethylethyl)-oxiranepropanamide.

16. The method according to claim 13 wherein the active material is 2-(3,5-dichlorophenyl)-α,α-difluorooxiranepropanamide.

17. The method according to claim 13 wherein the active material is α,α-dichloro-2-(3-chlorophenyl)oxiranepropanamide.

18. The method according to claim 18 wherein the active material is α,α-dichloro-N-(phenylmethyl)-2-(3-(trifluoromethyl)phenyl)oxiranepropanamide.

* * * * *